United States Patent [19]

Gerster

[11] 4,456,606

[45] Jun. 26, 1984

[54] SUBSTITUTED NAPHTHO[IJ]QUINOLIZINES

[75] Inventor: John F. Gerster, Woodbury, Minn.

[73] Assignee: Minnesota Mining and Manufacturing Company, St. Paul, Minn.

[21] Appl. No.: 376,540

[22] Filed: May 10, 1982

[51] Int. Cl.$^3$ ............................................ C07D 471/04
[52] U.S. Cl. ...................... 424/258; 546/71; 546/110
[58] Field of Search ................... 546/71, 110; 424/258

[56] References Cited

U.S. PATENT DOCUMENTS 3,896,131  7/1975  Gerster .............................. 424/258

OTHER PUBLICATIONS

Chemical Abstracts 55, 24747e.
Chem. Pharm. Bull. (Tokyo) 9, 226, (1961).

Primary Examiner—Paul M. Coughlan, Jr.
Attorney, Agent, or Firm—Donald M. Sell; James A. Smith; Robert W. Sprague

[57] ABSTRACT

1,2-dihydron-7-oxo-3H,5H-naphtho[1,2,3-ij]quinolizine-6-carboxylic acids are disclosed as active antimicrobial agents as are pharmaceutically acceptable esters, amides, acyl halides and salt derivatives thereof. Intermediates and synthetic processes are also disclosed.

11 Claims, No Drawings

SUBSTITUTED NAPHTHO[IJ]QUINOLIZINES

TECHNICAL FIELD

This invention relates to derivatives of the heterocyclic system known as naphtho[1,2,3-ij]quinolizine. More specifically it relates to 1,2-dihydro-7-oxo-3H,5H-naphtho[1,2,3-ij]quinolizine-6-carboxylic acids and esters, amides, acyl halides and salt derivatives thereof and the use of several of these compounds as antimicrobial agents. Intermediates for the preparation of the compounds and synthetic processes are also included within the scope of the invention.

BACKGROUND ART

The 3H,5H-naphtho[1,2,3-ij]quinolizine ring system has not previously been reported. The Ring Index lists a number of tetracyclic systems containing one nitrogen atom common to two of the rings. One example of a naphtho[1,2,3-ij]quinolizine is recorded, that being 1H,5H-naphtho[1,2,3-ij]quinolizine, found in Chem. Pharm. Bull. (Tokyo) 9, 226 (1961), Chemical Abstracts 55, 24747e.

DESCRIPTION OF THE INVENTION

This invention relates to 1,2-dihydro-7-oxo-3H,5H-naphtho[1,2,3-ij]quinolizine-6-carboxylic acids which may optionally be substituted at the 3 position by lower alkyl and on the naphtho ring, i.e., at the 9, 10, 11 and 12 positions by lower alkyl, lower alkoxy, or halogen. This invention also relates to pharmaceutically acceptable esters, amides, acyl halides and salts of the foregoing. The structure and numbering system for the 1,2-dihydro-7-oxo-3H,5H-naphtho[1,2,3-ij]quinolizine heterocyclic system are shown below:

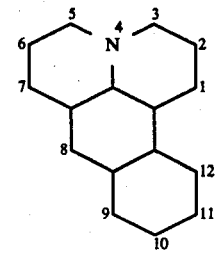

The carboxylic acid compounds of the invention may be represented by the following Formula I

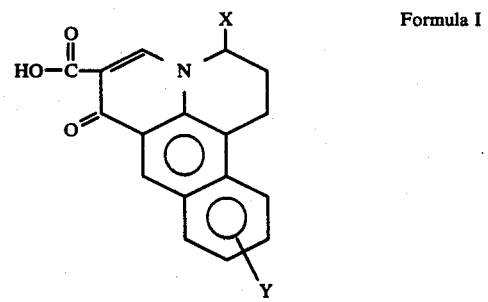

Formula I wherein:

X is hydrogen or lower alkyl; and

Y is hydrogen, lower alkyl, lower alkoxy or halogen. As used in the specification and claims, the term "lower" in connection with the terms "alkyl" or "alkoxy" designates moieties comprising 1 to 4 carbon atoms.

Pharmaceutically acceptable salts such as alkali metal, alkaline earth, aluminum, iron and other metal and quaternary amine salts of the acids of the invention are substantially equivalents to the acids, and in some cases may even offer advantages in absorption, formulation and the like.

The 1,2-dihydro-7-oxo-3H,5H-naphtho[1,2,3-ij]quinolizine-6-carboxylic acids of Formula I may be prepared by the following Procedure A wherein X and Y are as previously defined:

Procedure

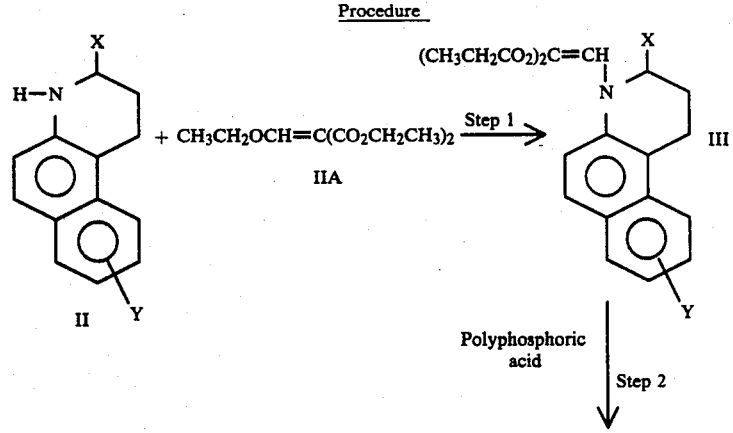

Procedure

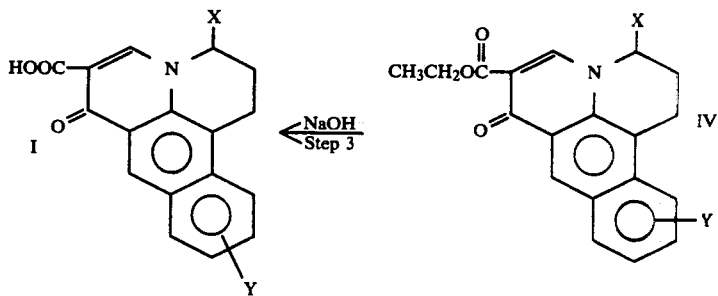

In step 1 of Procedure A, a dialkyl ethoxymethylenemalonate (IIA) is condensed with a 1,2,3,4-tetrahydrobenzo[f]quinoline of Formula II by heating at 100° to 250° C., and preferably at 150° to 200° C., for one to five hours in the absence of solvent. Actually the ester IIA may be any simple diester of ethoxymethylenemalonic acid, although lower alkyl esters, such as the diethyl ester shown here, are preferred. The product of step 1 is the N-(2,2-biscarbalkoxy)vinyltetrahydrobenzo[f]quinoline of Formula III which may be used directly in step 2 without isolation and purification thereof.

Polyphosphoric acid is added in step 2 to the reaction mixture containing the N-(2,2-biscarbalkoxy)vinyltetrahydrobenzo[f]quinoline of Formula III, the resulting mixture being heated to about 70° to 140° C., and preferably to 70° to 120° C. to effect a condensation reaction to form the ethyl ester of 1,2-dihydro-7-oxo-3H,5H-naphtho[1,2,3-ij]quinolizine-6-carboxylic acid (Formula IV).

In step 3, the ethyl ester of Formula IV is saponified with excess base for example alcoholic potassium hydroxide or aqueous sodium hydroxide, the reaction mixture being heated at about 90° C. for about 1 to 2 hours. The reaction product in step 3 is the 1,2-dihydro-7-oxo-3H,5H-naphtho[1,2,3-ij]quinolizine-6-carboxylic acid of Formula I.

The intermediate compounds of Formula II may be prepared from known precursors by Procedure B or by Procedure C as follows:

Procedure B

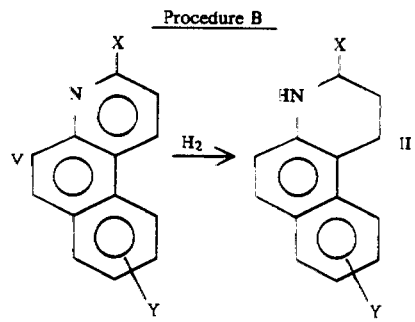

In the above reaction, conventional catalytic reduction methods employing, for example, rhodium on carbon or platinum on carbon catalysts may be used. The reaction is generally conducted in a suitable solvent such as ethanol.

Procedure C

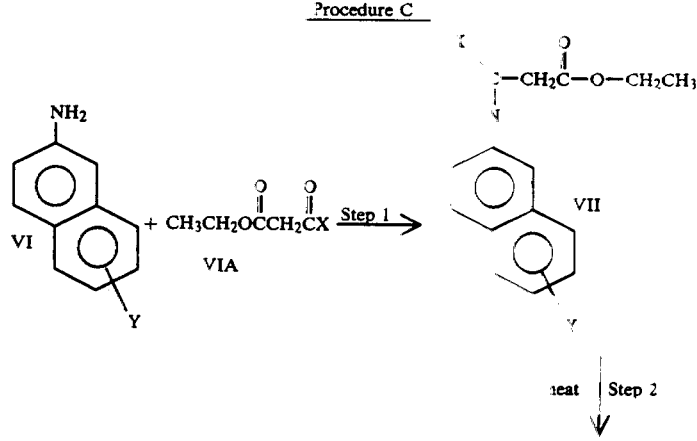

Procedure C

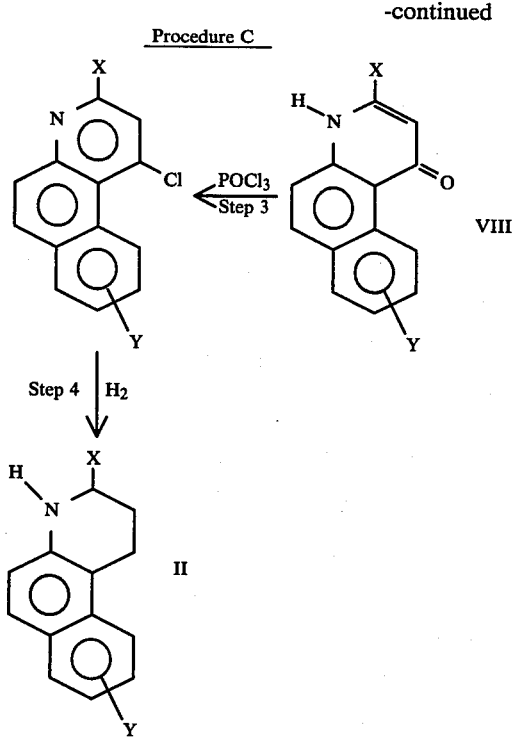

In Step 1 of Procedure C, a β-aminonaphthalene of Formula VI is reacted with the indicated ester of formula VIA. The reaction may be conducted in the absence of solvent. Alternatively, the reaction may be conducted in the presence of solvent and an acid catalyst such as p-toluenesulfonic acid. The compound of Formula VII obtained in Step 1 is then heated for 0.5–4 hours at reflux in a high boiling solvent such as that available under the trade designation "Dowtherm A" (a mixture of biphenyl and phenoxybenzene, commercially available from Dow Chemical Company) to form the compound of Formula VII. The adduct obtained in Step 1 may be isolated prior to conducting Step 2 or the entire reaction product of Step 1 may be used directly in Step 2. In Step 3, the compound of Formula VIII is reacted with phosphorus oxychloride to form the compound of Formula IX. Finally, the compound of Formula IX is reduced in Step 4 using a rhodium on charcoal catalyst in ethanol in the presence of one equivalent of sodium acetate per equivalent of the compound of Formula IX.

Certain of the esters of the invention (IV) are intermediates in the preparation of the carboxylic acids (I). These and other esters of the invention can also be prepared from the acids(I) using conventional synthetic procedures.

Acyl chloride derivatives of the carboxylic acids of Formula I are prepared from salts of the acids themselves by reaction with thionyl chloride. The acyl chlorides are also conveniently prepared directly from the acids by reaction with thionyl chloride.

The acyl chlorides which may be prepared as described above are useful for preparing the other derivatives of the carboxylic acids of Formula I. For example, the acyl chlorides are useful for preparing esters by reaction with a suitable alchohol or preparing amides by reaction with a suitable amine. Further, the acyl chlorides may be hydrolyzed to form the acids themselves.

Pharmaceutically-acceptable carboxylate salts of the free acid compounds of the invention are readily prepared by reaction of the acid with a base and subsequent evaporation of the reaction product to dryness. The base may be organic, e.g., sodium methoxide or an amine, or inorganic, e.g., sodium hydroxide. Alternatively, a carboxylate salt, e.g. the sodium salt, may be displaced by a second cation, e.g. calcium or magnesium, when the salt of the second cation is more insoluble in a selected solvent such as water.

The anti-microbial activity of the compounds of the present invention was detected by the plate dilution method for bacterial susceptibility to antibiotics. The culture medium employed permits susceptibiity testing of fastidious microorganisms to antibiotics, sulfonamides and other chemotherapeutic agents. This is tryptone soy agar (oxoid) of the following composition:

| | |
|---|---|
| oxoid tryptone | 15 g. |
| oxoid soy peptone | 5 g. |
| sodium chloride | 5 g. |
| oxoid agar-agar no. 3 | 15 g. |
| water | 1 liter |

The activity of the compounds was determined both in the absence and presence of ten percent horse serum. The amount of a compound required to give complete inhibition, partial inhibition or no inhibition of microbial growth on the agar plates was determined. Compound was added to the agar to give concentrations of zero, one, ten and one hundred milligrams per liter. Ten percent horse serum was then added if desired. Aliquots of broth culture of each of nine species of microorganisms were inoculated onto the agar plates containing the various compound concentrations. The plates were incubated at 37° C. in a ten percent carbon dioxide atmosphere for 18 to 24 hours. The microbial growth on each plate was read visually and minimal inhibitory concentrations were recorded.

The microorganisms used for this test were:
1. *Staphylcoccus aureus*
2. *Bacillus subtilis*
3. *Pseudomonas aeruginosa*
4. *Escherichia coli*
5. Streptococcus sp.*
6. *Aspergillus niger*
7. *Candida albicans*
8. *Mima polymorpha*
9. *Herellea vaginicola*

*Strains isolated from dental caries in rats or hamsters at the National Institute of Dental Health and grown in PFY or APT Agar.

All of the compounds of the invention are active versus one or more of the above microorganisms. Some of the compounds of the invention are also active versus anaerobic bacteria such as *Clostridium welchii*.

The preferred species of the invention (infra) possess broad spectrum gram-positive and gram-negative antibacterial activity. Such broad spectrum activity is demonstrated on the basis of the activity shown against selected indicator bacterial species since it would be impractical to screen against all bacteria.

The most preferred compound of the invention is particularly efficacious versus staphylococci as indicated by its high activity versus *Staphylococcus aureus*. It has also shown high activity versus *E. coli* and *Bacillus subtilis*.

All of the compounds of the invention are active versus microorganisms in vitro. In vitro activity is useful in itself, since anti-microbial agents may be used for disinfecting and sterilizing, for example medical and dental equipment as components of disinfecting solutions. In vitro activity is also an indicator of possible in vivo activity in animals.

The toxicity of the compounds of the invention has been examined, and a fair to excellent therapeutic ratio is present based on the data presently available for the preferred compounds.

The presently preferred compounds of the invention have a broad spectrum of antimicrobial activity and a good therapeutic ratio ($LD_{50}/ED_{50}$). These compounds are:
ethyl 1,2-dihydro-3-methyl-7-oxo-3H,5H-naphtho[1,2,3-ij]quinolizine-6-carboxylate and 1,2-dihydro-3-methyl-7-oxo-3H,5H-naphtho[1,2,3-ij]quinolizine-6-carboxylic acid.

The most preferred compound of the invention is presently 1,2-dihydro-3-methyl-7-oxo-3H,5H-naphtho[1,2,3-ij]quinolizine-6-carboxylic acid. This compound is preferred because of very high in vitro activity and clearly demonstrated low absorption from the digestive tract into blood and urine. This combination of properties provides utility for enteric infections localized in the gastrointestinal tract, for example dysentery, cholera, colibacillosis and secondary invasion of the mucosal lining.

The compounds of the invention may be formulated by incorporating them into conventional pharmaceutical carrier materials, either organic or inorganic, which are suitable for oral or intraperitoneal application.

The amount of compound to be used for treatment of a microbial infection will be an effective amount less than a toxic amount. The amount to be administered to control an infection will depend on the species, sex, weight, physical condition and many other factors, but this judgment is well within the skill of the medical art. Usually the amount will be less than 100 mg./kg/ per dose.

It is known to the art that anti-microbial agents are used as growth promoters in various animal and bird species. Although it has not yet been shown clinically that the use of the compounds of this invention will promote growth in animals or birds, it appears from the outstanding anti-microbial activity that the compounds will be growth-promoters.

The following examples are provided to illustrate the synthetic methods useful to obtain compounds of the invention. They are not intended to be limiting on the invention as described hereinabove and specifically claimed.

EXAMPLE 1

Ethyl 1,2-Dihydro-3-methyl-7-oxo-3H,5H-naphtho[1,2,3-ij]quinolizine-6-carboxylate A mixture of diethyl ethoxymethylenemalonate (17.3 g., 0.08 mole) and 3-methyl-1,2,3,4-tetrahydrobenzo[f]quinoline (prepared by reduction of 1-chloro-3-methylbenzo[f]quinoline with rhodium on carbon) (15.8 g., 0.08 mole) was heated to 200° C., then slowly cooled to about 170° C. and maintained at that temperature for about three hours. After cooling to ambient temperature, polyphosphoric acid (100 g.) was added and the mixture was heated at 90° C. with manual stirring. The temperature was permitted to rise gradually to about 110° C. and the mixture was observed to foam. After the foam subsided, the mixture was poured into hot water with stirring. An oil formed which became a yellow solid when cooled. Recrystallization from methanol provided ethyl 1,2-dihydro-3-methyl-7-oxo-3H,5H-naphtho[1,2,3-ij]quinolizine-6-carboxylate as a pale yellow solid, m.p. 178°–180° C.

| Analysis: | % C | % H | % N |
|---|---|---|---|
| Calculated for $C_{20}H_{19}NO_3$: | 74.7 | 6.0 | 4.4 |
| Found: | 74.9 | 5.8 | 4.3 |

EXAMPLE 2

1,2-Dihydro-3-methyl-7-oxo-3H,5H-naphtho[1,2,3-ij]quinolizine-6-carboxylic Acid

A solution of ethyl 1,2-dihydro-3-methyl-7-oxo-3H,5H-naptho[1,2,3-ij]quinolizine-6-carboxylate (12.5 g., 0.0389 mole) in ethanol (175 ml.) was treated with a solution of potassium hydroxide (4.3 g., 0.0786 mole) in ethanol (175 ml.). The mixture was then heated to its reflux temperature and maintained at reflux for two hours. The intermediate formed was potassium 1,2-dihydro-3-methyl-7-oxo-3H,5H-naphtho[1,2,3-ij]quinolizine-6-carboxylate. The mixture was diluted with hot water (350 ml.) then acidified with hydrochloric acid. The precipitate was collected by filtration, washed with a fifty percent ethanol-water mixture and dried. The solid was recrystallized from N,N-dimethylformamide to give yellow needles of 1,2-dihydro-3-methyl-7-oxo-3H,5H-naphtho[1,2,3-ij]quinolizine-6-carboxylic acid, m.p. 270°–273° C.

| Analysis: | % C | % H | % N |
|---|---|---|---|
| Calculated for $C_{18}H_{15}NO_3$: | 73.7 | 5.2 | 4.8 |

| Analysis: | | % C | % H | % N |
|---|---|---|---|---|
| | Found: | 73.8 | 5.0 | 4.8 |

EXAMPLES 3-6

The following Table (I) describes several compounds of the invention which may be made using the process of the invention, and indicates which known starting materials may be used to prepare the compounds of the invention. The procedures which may be employed for obtaining the intermediate from the starting material (Procedures B or C) and for obtaining the final product from the intermediate (Procedure A) are those which have been described previously herein.

1,2-dihydro-3-methyl-7-oxo-3H,5H-naphtho[1,2,3-ij]quinolizine-6-carboxylic acid (the compound prepared in Example 2) was determined using the standard plate dilution method described hereinabove. The tests were run both in the absence (Column A) and in the presence (Column B) of horse serum as described hereinabove. The results (recorded at the minimum concentrations in terms of milligrams of the active antimicrobial agent per liter which provide partial or complete inhibition of the growth of the indicated microorganisms are shown in the table below:

| | Compound of Example 1 | | Compound of Example 2 | |
|---|---|---|---|---|
| Organism | A | B | A | B |
| Streptococcus sp. | 10 | 10 | 100 | 100 |
| Staphylococcus aureus | 1 | 1 | 1 | 1 |
| Bacillus subtilis | 1 | 1 | 1 | 1 |
| Escherichia coli | $1^a$ | $1^a$ | 1 | 1 |
| Pseudomonas aeruginosa | >100 | >100 | >100 | >100 |

TABLE I

Example Number / Known Starting Material / Intermediate / Final Product 3, 4, 5, 6 — structural diagrams showing conversion of known starting materials (substituted naphthylamines/quinolines) via Procedure B or C to intermediates, then via Procedure A to final products (naphtho[1,2,3-ij]quinolizine-6-carboxylic acid derivatives).

EXAMPLE 7

The antibacterial activity of ethyl 1,2-dihydro-3-methyl-7-oxo-3H,5H-naphtho[1,2,3-ij]quinolizine-6-carboxylate (the compound prepared in Example 1) and -continued

| Organism | Compound of Example 1 | | Compound of Example 2 | |
|---|---|---|---|---|
| | A | B | A | B |
| *Mima polymorpha* | >100 | >100 | >100 | >100 |
| *Herellea vaginicola* | 10 | 10[a] | 10 | 10 |
| *Aspergillus niger* | >100 | >100 | >100 | >100 |
| *Candida abicans* | >100 | >100 | >100 | >100 |

[a] partial inhibition

It is seen that the above-described compounds of the present invention exhibit suitable biological activity against a variety of microorganisms.

What is claimed is:

1. A compound of the formula

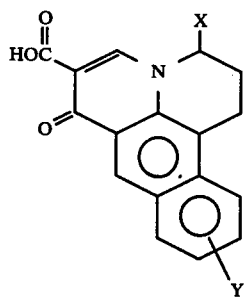

wherein X is hydrogen or lower alkyl and Y is hydrogen, lower alkyl, lower alkoxy or halogen; or a lower alkyl ester, acyl chloride or pharmaceutically-acceptable carboxylate salt thereof.

2. A compound according to claim 1, wherein X is methyl.

3. A compound according to claim 1, wherein Y is hydrogen.

4. The compound 1,2-dihydro-3-methyl-7-oxo-3H,5H-naphtho[1,3,4-ij]quinolizine-6-carboxylic acid or a lower alkyl ester, acyl chloride, or pharmaceutically-acceptable carboxylate salt thereof.

5. A method for inhibiting or arresting the growth of microbes comprising contacting said microbes with a 1,2-dihydro-7-oxo-3H,5H-naphtho[1,2,3-ij]quinolizine-6-carboxylic acid according to claim 1 or a lower alkyl ester or pharmaceutically-acceptable carboxylic salt thereof according to claim 1 in an amount sufficient to inhibit the growth of said microbes.

6. A method for inhibiting or arresting the growth of microbes comprising contacting said microbes with a compound according to claim 4 in an amount sufficient to inhibit the growth of said microbes.

7. An antimicrobial pharmaceutical composition comprising an effective amount of a 1,2-dihydro-7-oxo-3H,5H-naphtho[1,2,3-ij]quinolizine-6-carboxylic acid according to claim 1 or a lower alkyl ester or pharmaceutically-acceptable carboxylate salt according to claim 1 and a pharmaceutically-acceptable extending medium.

8. A process for the preparation of an ester of a compound of the formula:

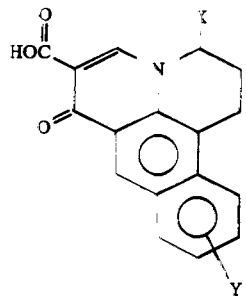

wherein X is hydrogen or lower alkyl and Y is hydrogen, lower alkyl, lower alkoxy or halogen; comprising the steps of (1) reacting a 1,2,3,4-tetrahydrobenzo[f]quinoline with a diester of ethoxymethylenemalonic acid at a temperature between about 100° and 250° to form a N-(2,2-biscarbalkoxy)vinyltetrahydrobenzo[f]quinoline, and (2) reacting said N-(2,2-biscarbalkoxy)vinyltetrahydrobenzo[f]quinoline in polyphosphoric acid at about 70° to 140° C. to form an ester of 1,2-dihydro-7-oxo-3H,5H-naphtho[1,2,3-ij]-quinolizine-6-carboxylic acid.

9. A process for the preparation of a compound of the formula:

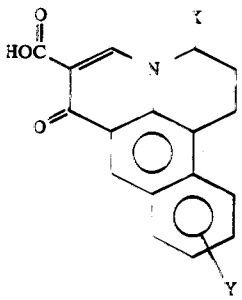

wherein X is hydrogen or lower alkyl and Y is hydrogen, lower alkyl, lower alkoxy or halogen; comprising the steps of (1) reacting a 1,2,3,4-tetrahydrobenzo[f]quinoline with a diester of ethoxymethylenemalonic acid at a temperature between about 100° and 250° C. to form a N-(2,2-biscarbalkoxy)vinyltetrahydrobenzo[f]quinoline, (2) reacting said N-(2,2-biscarbalkoxy)vinyltetrahydrobenzo[f]quinoline in polyphosphoric acid at about 70° to 140° C. to form an ester of 1,2-dihydro-7-oxo-3H,5H-naphtho[1,2,3-ij]quinolizine-5-carboxylic acid, and (3) reacting said ester of 1,2-dihydro-7-oxo-3H,5H-naphtho[1,2,3-ij]quinolizine-6-carboxylic acid with an inorganic base to hydrolyze the ester moiety.

10. A process in accordance with claim 8 or 9, wherein said 1,2,3,4-tetrahydrobenzo[f]quinoline is reacted with said diester of ethoxymethylenemalonic acid at a temperature between about 150° and 200° C. and said N-(2,2-biscarbalkoxy)vinyltetrahydrobenzo[f]quinoline is reacted with said polyphosphoric acid at a temperature between 70° and 120° C.

11. The compound of the formula:

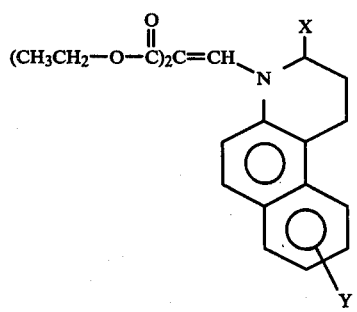
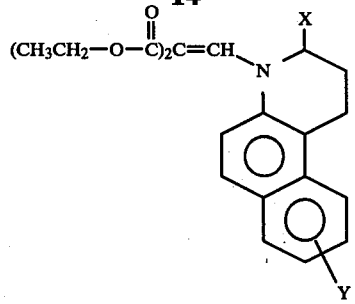
wherein X is hydrogen or lower alkyl and Y is hydrogen, lower alkyl, lower alkoxy or halogen.
* * * * *
wherein X is hydrogen or lower alkyl and Y is hydrogen, lower alkyl, lower alkoxy or halogen.
* * * * *